United States Patent
Yui et al.

(10) Patent No.: US 9,292,762 B2
(45) Date of Patent: Mar. 22, 2016

(54) REGION EXTRACTION SYSTEM

(71) Applicant: Hitachi, Ltd., Tokyo (JP)

(72) Inventors: Shuntaro Yui, Tokyo (JP); Kazuki Matsuzaki, Tokyo (JP); Junichi Miyakoshi, Tokyo (JP)

(73) Assignee: HITACHI, LTD., Tokyo (JP)

( * ) Notice: Subject to any disclaimer, the term of this patent is extended or adjusted under 35 U.S.C. 154(b) by 58 days.

(21) Appl. No.: 14/377,316

(22) PCT Filed: Dec. 21, 2012

(86) PCT No.: PCT/JP2012/083192
§ 371 (c)(1),
(2) Date: Aug. 7, 2014

(87) PCT Pub. No.: WO2013/121679
PCT Pub. Date: Aug. 22, 2013

(65) Prior Publication Data
US 2015/0049935 A1   Feb. 19, 2015

(30) Foreign Application Priority Data

Feb. 13, 2012 (JP) ................. 2012-027975

(51) Int. Cl.
*G06K 9/00* (2006.01)
*G06K 9/46* (2006.01)
(Continued)

(52) U.S. Cl.
CPC ............ *G06K 9/4661* (2013.01); *A61B 5/4244* (2013.01); *G06T 7/0012* (2013.01); *G06T 7/0081* (2013.01); *G06K 2009/4666* (2013.01); *G06T 2207/20076* (2013.01); *G06T 2207/30056* (2013.01)

(58) Field of Classification Search
CPC ............ G06K 9/00127; G06K 9/4661; G06K 9/6231; G06K 9/6251; G06K 9/6255; G06K 2209/4666; G06T 5/50; G06T 7/0012; G06T 7/0014; G06T 7/0075; G06T 7/0081; G06T 2207/10132; G06T 2207/20076; G06T 2207/20081; G06T 2207/30004; G06T 2207/30024; G06T 2207/30008; G06T 2207/30056; A61B 1/00009; A61B 1/0005; A61B 1/00055; A61B 1/04; A61B 1/043; A61B 5/0033; A61B 5/4244; A61B 8/5215; A61B 8/5223; A61B 12/006; G06F 19/321; G06F 19/345; G01N 15/147; H04N 13/0425; G06Q 50/22

See application file for complete search history.

(56) References Cited

U.S. PATENT DOCUMENTS

2010/0250275 A1* 9/2010 Sakagawa ............. G06F 19/321
705/2

FOREIGN PATENT DOCUMENTS

JP   2009-082452   4/2009

OTHER PUBLICATIONS

A. Shimizu; T. Kawamura; H. Kobatake, Proposal of computer-aided detection system for three dimensional CT images of liver cancer, CARS 2005;1281; 1157-1262.
(Continued)

*Primary Examiner* — Jose Couso
(74) *Attorney, Agent, or Firm* — Baker Botts L.L.P.

(57) ABSTRACT

Provided is a region extraction system that uses an image data analysis process, which has overcome the problem of false positives in region extraction and assists in more accurate region extraction. A luminance distribution-analyzing unit (105) is used to determine a parameter of unknown quantity for extracting a region of interest. The luminance distribution-analyzing unit (105) searches a luminance distribution management database (106) for a region, which has a luminance distribution similar to the region of interest and is easily extracted, as a similar area. The region of the similar area is extracted using a region extraction pre-processing unit (107) and the value of the parameter of unknown quantity is determined on the basis of an image feature value calculated from the region extraction results.

9 Claims, 18 Drawing Sheets

(51) Int. Cl.
*G06T 7/00* (2006.01)
*A61B 5/00* (2006.01)

(56) References Cited

OTHER PUBLICATIONS

M.A. Selver, C. Guneyt, Semiautomatic Transter Function Initialization for Abdominal Visualization Using Self-Generating Hierarchical Radial Basis Functon Networks, IEEE Trans. 2009;15; 3; 395-409.

Y. Shang, A. Markova, R. Deklerck, E. Nyssen, X. Yang, J.D. Mey, Liver segmentation by an active contour model with embedded Gaussian mixture model based classifiers, SPIE 2010; 7723; pp. 772313-1-772313-7.

* cited by examiner

ALGORITHM DISSECTION MANAGEMENT TABLE

| ALGORITHM | PARAMETER PATTERN | PHASE | EXTRACTED BIOLOGICAL TISSUE | BIOLOGICAL TISSUE CODE |
|---|---|---|---|---|
| Level Set | 1 | ARTERIAL PHASE | INTRAHEPATIC BLOOD VESSEL | 001-1 |
| Level Set | 1 | ARTERIAL PHASE | PORTAL VEIN | 001-2 |
| Level Set | 1 | ARTERIAL PHASE | HCC | 001-3 |
| Level Set | 2 | ARTERIAL PHASE | HCC | 001-3 |
| Level Set | 3 | ARTERIAL PHASE | NECROSIS | 001-7 |
| Graph Cut | 4 | ARTERIAL PHASE | LIVER | 001 |
| ... | ... | ... | ... | ... |

602

PARAMETER PATTERN TABLE

| PARAMETER PATTERN | GRADIENT | LUMINANCE | LUMINANCE MAXIMUM VALUE | LUMINANCE MINIMUM VALUE | LINE REMOVAL | LINE EXTRACTION |
|---|---|---|---|---|---|---|
| 1 | 1 | 1 | 150 | 50 | 1 | — |
| 2 | 1 | 1 | 150 | 50 | 0 | — |
| 3 | 1 | 1 | ? | ? | 1 | — |
| 4 | 1 | 1 | 60 | 20 | 1 | — |
| ... | ... | ... | ... | ... | ... | ... |

FIG. 10

LUMINANCE DISTRIBUTION MANAGEMENT TABLE

| CLASS | PHASE | BIOLOGICAL TISSUE | BIOLOGICAL TISSUE CODE |
|---|---|---|---|
| 1 | ARTERIAL PHASE | INTRAHEPATIC BLOOD VESSEL | 001-1 |
| 1 | ARTERIAL PHASE | PORTAL VEIN | 001-2 |
| 1 | ARTERIAL PHASE | HCC | 001-3 |
| 1 | ARTERIAL PHASE | KIDNEY | 003 |
| 2 | ARTERIAL PHASE | HEPATOCYTE | 001-4 |
| 2 | ARTERIAL PHASE | LIVER MARGINAL REGION | 001-5 |
| 3 | ARTERIAL PHASE | CYST | 001-6 |
| 3 | ARTERIAL PHASE | NECROSIS | 001-7 |
| 4 | ARTERIAL PHASE | LIVER | 001 |
| 4 | ARTERIAL PHASE | SPLEEN | 002 |
| 5 | DELAYED PHASE | INTRAHEPATIC BLOOD VESSEL | 001-1 |
| 5 | DELAYED PHASE | PORTAL VEIN | 001-2 |
| 6 | DELAYED PHASE | HCC | 001-3 |
| 7 | DELAYED PHASE | HEPATOCYTE | 001-4 |
| 7 | DELAYED PHASE | LIVER MARGINAL REGION | 001-5 |
| 8 | DELAYED PHASE | CYST | 001-6 |
| 8 | DELAYED PHASE | NECROSIS | 001-7 |
| ... | ... | ... | ... |

FIG. 13

ORDER MANAGEMENT TABLE

| ORDER ID | REQUESTED DATE | REQUESTER | NAME OF PATIENT | OBJECT AREA | NAME OF SUSPICIOUS DISEASE |
|---|---|---|---|---|---|
| 001 | 2011/7/1 | Ada Bo | P001 | LIVER | HCC |
| 002 | 2011/7/2 | Cda Do | P002 | LIVER | METASTATIC LIVER CANCER |
| ... | ... | ... | ... | ... | ... |

FIG. 16

ALGORITHM DISSECTION MANAGEMENT TABLE

| ALGORITHM | PARAMETER PATTERN | PHASE | EXTRACTED BIOLOGICAL TISSUE | BIOLOGICAL TISSUE CODE | FALSE POSITIVE RATE |
|---|---|---|---|---|---|
| Level Set | 1 | ARTERIAL PHASE | INTRAHEPATIC BLOOD VESSEL | 001-1 | 0.3 |
| Level Set | 1 | ARTERIAL PHASE | PORTAL VEIN | 001-2 | 0.3 |
| Level Set | 1 | ARTERIAL PHASE | HCC | 001-3 | 0.3 |
| Level Set | 2 | ARTERIAL PHASE | HCC | 001-3 | 0.2 |
| Level Set | 3 | ARTERIAL PHASE | NECROSIS | 001-7 | 0.1 |
| Graph Cut | 4 | ARTERIAL PHASE | LIVER | 001 | 0.1 |
| Level Set | 5 | ARTERIAL PHASE | INTRAHEPATIC BLOOD VESSEL | 001-1 | 0.1 |
| Level Set | 5 | ARTERIAL PHASE | PORTAL VEIN | 001-2 | 0.1 |
| ... | ... | ... | ... | ... | ... |

PARAMETER PATTERN TABLE

| PARAMETER PATTERN | GRADIENT | LUMINANCE | LUMINANCE MAXIMUM VALUE | LUMINANCE MINIMUM VALUE | LINE REMOVAL | LINE EXTRACTION |
|---|---|---|---|---|---|---|
| 1 | 1 | 1 | 150 | 50 | 1 | — |
| 2 | 1 | 1 | 150 | 50 | 0 | — |
| 3 | 1 | 1 | ? | ? | 1 | — |
| 4 | 1 | 1 | 60 | 20 | 1 | — |
| 5 | 1 | 1 | 150 | 50 | 0 | 1 |
| ... | ... | ... | ... | ... | ... | ... |

REGION EXTRACTION SYSTEM

TECHNICAL FIELD

The present invention relates to an analysis processing system for medical image data.

BACKGROUND ART

The number of images to be acquired in one checkup has been enormously increased and loads on diagnosticians and radiologists have been more and more increased with development of medical image diagnostic devices. Since it becomes possible to acquire a large number of images, in particular, in an X-ray CT (Computed Tomography) device, an immense amount of labor has become necessary for a doctor in tumor diagnosis. Since an increase in labor taken for such diagnosis may induce an oversight and an erroneous diagnosis, it is demanded to reduce it as much as possible. Therefore, a technology (CAD: Computer Aided Detection) that automatically extracts a region concerned such as a tumor and so forth and a device with that technology loaded are proposed.

In Non-Patent Literature 1, for the purpose of extracting a liver tumor, a technique of applying a Region Growing method of extracting a point which is the highest in X-ray absorption coefficient (hereinafter, a luminance value) by using an image to which a liner pattern extraction filter has been applied and setting the extracted point as a seed to an original image is proposed.

In Non-Patent Literatures 2 and 3, techniques of generating a histogram distribution of the X-ray absorption coefficient (hereinafter, the luminance value) from the original image, obtaining a parameter of each distribution by assuming a luminance value distribution of a region concerned to be a Gaussian distribution and extracting the region concerned on the basis of the obtained luminance value distribution are proposed.

In Patent Literature 1, a technology of selecting an image processing procedure and parameters thereof which have been set in advance from image data and image incidental information and executing it.

CITATION LIST

Patent Literature

PTL 1: Japanese Patent Application Laid-Open No. 2009-82452

Non-Patent Literatures

Non-Patent Literature 1: A. Shimizu, T. Kawamura, H. Kobatake, Proposal of computer-aided detection system for three dimensional CT images of liver cancer, CARS 2005; 1281; 1157-1262

Non-Patent Literature 2: M. A. Selver, C. Guneyt, Semiautomatic Transfer Function Initialization for Abdominal Visualization using Self-Generating Hierachical Radial Basis Function Networks, IEEE Trans. 2009; 15; 3; 395-409

Non-Patent Literature 3: Y. Shang, A. Markova, R. Deklerck, E. Nyssen, X. Yang, J. D. Mey, Liver segmentation by an active contour model with embedded Gaussian mixture model based classifiers. SPIE 2010; 7723; 772313

SUMMARY OF INVENTION

Technical Problem

In many cases, the luminance value distribution of the region concerned is unknown. For example, in a contrast CT checkup of a liver cancer, in an arterial phase to be photographed in about 30 seconds after rapid intravenous injection of a contrast medium, the contrast medium is taken into an object tissue and is highly absorbed, and the image contrast of the object tissue becomes clear. However, since the contrast medium rapidly diffuses and photographing timings are often made different, there is no guarantee that the luminance value distributions of the region concerned will be always made the same. Therefore, in the aforementioned prior art, false positives are increased by extracting a region that a user does not intend and it has caused deterioration of extraction precision.

In the case of the aforementioned Non-Patent Literature 1, it is not assumed that there exists a plurality of tumors. In addition, since the detailed luminance distribution is unknown and region extraction is performed only on the basis of a luminance gradient and a linear pattern, there are cases when the problem of false positives occurs. In the case of the aforementioned Non-Patent Literatures 2 and 3, since regions which are different in luminance value such as, for example, the hepatocyte, a liver marginal part, a cyst, a tumor, a necrosis, a blood vessel and so forth are present adjacently in the liver alone, estimation of the accurate luminance value distribution was difficult. In the aforementioned Patent Literature 1, the images which have been taken a plurality of times are necessary in order to determine an appropriate parameter and the accompanying burden on a patient occurs.

Since the estimation of the detailed luminance distribution is difficult for the conventionally disclosed technologies as just described, it was impossible to overcome the problem of false positives in region extraction. Therefore, the problem to be solved by the present invention is to provide a region extraction system by analysis processing of image data that assists in more accurate region extraction by overcoming the problem of false positives in region extraction.

Solution to Problem

In order to solve the above-mentioned problems, there is provided a system that extracts a region of interest from an image, the region extraction system, having an input unit that accepts inputs of the aforementioned region of interest and an object image, an algorithm management dissection database that stores an optimum algorithm and an unknown quantity including parameter for extracting the aforementioned region of interest, a region extraction unit that acquires the aforementioned algorithm and the aforementioned parameter stored in the aforementioned algorithm management dissection database with entry of the aforementioned region of interest and the aforementioned object image and executes region extraction processing for the aforementioned region of interest by applying the aforementioned algorithm and the aforementioned parameter so acquired to the aforementioned object image, a luminance distribution analyzing unit that outputs an unknown quantity parameter by calculating a luminance distribution of the aforementioned region of interest with entry of the aforementioned region of interest and the aforementioned object image as the inputs, a luminance distribution management database that stores similarity in luminance distribution of biological tissues, a region extraction pre-processing unit that performs pre-processing for obtaining the unknown quantity parameter with entry of the aforementioned object image, and the aforementioned algorithm and the aforementioned parameter stored in the aforementioned algorithm management dissection database and a display unit that displays a result of extraction, wherein in the aforementioned region extraction unit, in a case where the unknown quantity is included in the aforementioned parameter so input, an optimum value of the parameter is acquired from the aforementioned luminance distribution analyzing unit.

Advantageous Effects of Invention

According to the region extraction system of the present invention, when the luminance value distribution of a region concerned is to be estimated, it becomes possible to estimate the luminance value distribution of the region concerned with higher precision by using the luminance value distribution of a region which is similar to it in luminance value and is readily extracted and thereby the problem of false positives in region extraction can be overcome. Thereby, it becomes possible to facilitate region extraction and to implement more accurate region extraction. That is, it becomes possible to reduce the labor of the doctor in tumor diagnosis. In addition, it becomes possible to acquire the name of an area which will become the region concerned with no intervention of the user and it becomes possible to implement a reduction in entry work of the user by coordinating with an information system such as electronic medical records and so forth.

BRIEF DESCRIPTION OF DRAWINGS

FIG. 6 is a first example indicating an algorithm dissection management database of the region extraction system in the present invention.

FIG. 10 is a diagram indicating a luminance distribution management database of the region extraction system in the present invention.

FIG. 13 is a diagram indicating an electronic medical record database of the region extraction system in the present invention.

FIG. 16 is a second example indicating the algorithm dissection management database of the region extraction system in the present invention.]

DESCRIPTION OF EMBODIMENTS

In the following, best modes for embodying the present invention will be described.

Embodiment 1

Figure 1:
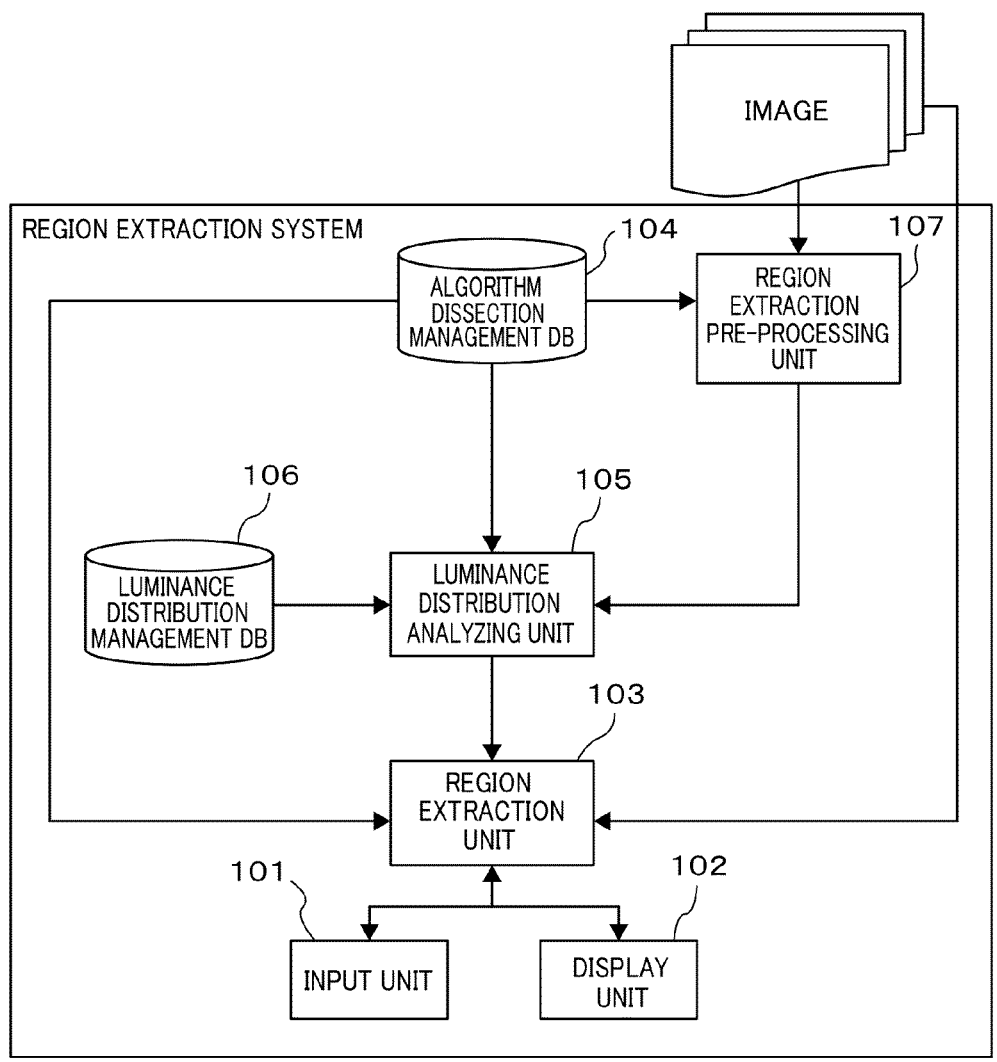
FIG. 1 is a first configuration diagram of a region extraction system in the present invention.

FIG. 1 is a configuration diagram of a region extraction system in the present invention. The region extraction system shown in FIG. 1 is configured by an input unit 101, a display unit 102, a region extraction unit 103, an algorithm dissection management database 104, a luminance distribution analyzing unit 105, a luminance distribution management database 106 and a region extraction pre-processing unit 107.

Figure 2:
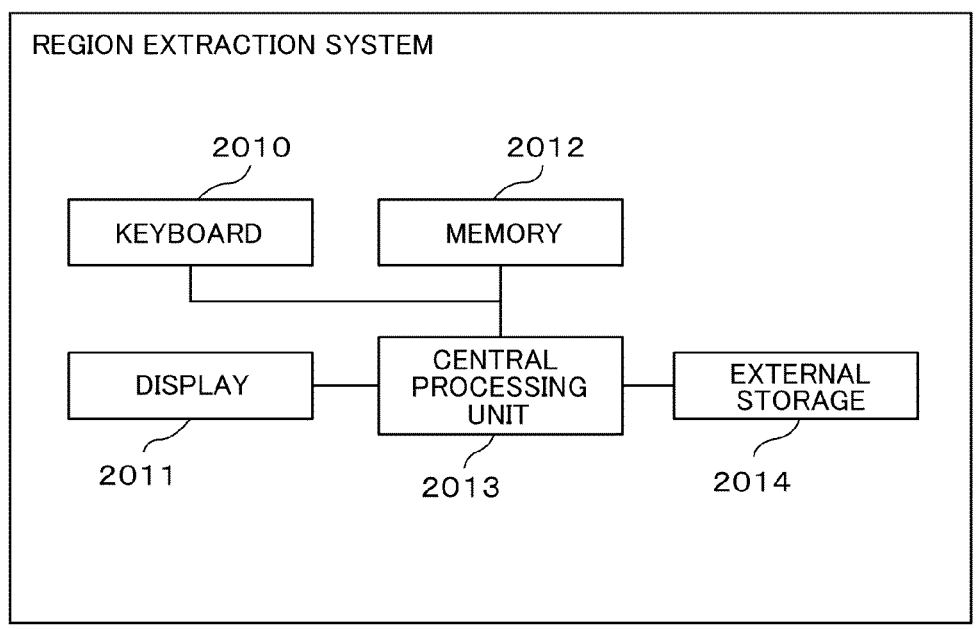
FIG. 2 is a hardware configuration diagram of the region extraction system in the present invention.

A hardware configuration of the present system will be described. A configuration diagram of hardware implementing the region extraction system in the present invention is shown in FIG. 2. The algorithm dissection management database 104 and the luminance distribution management database 106 are configured by an external storage 2014 and so forth represented by an HDD (Hard Disk Drive) device. The region extraction unit 103, the luminance distribution analyzing unit 105 and the region extraction pre-processing unit 107 can implement various kinds of processing by developing/starting a predetermined program in a central processing unit 201, a memory 2012 and so forth. The display unit 102 can be implemented by a monitor utilizing a liquid crystal display 2011, a CRT (Cathode-Ray Tube) and so forth. In addition, it may be output onto a medium such as paper and so forth. The input unit 101 can be implemented by a keyboard 2010, a mouse, a pen tablet and so forth.

Figure 3:
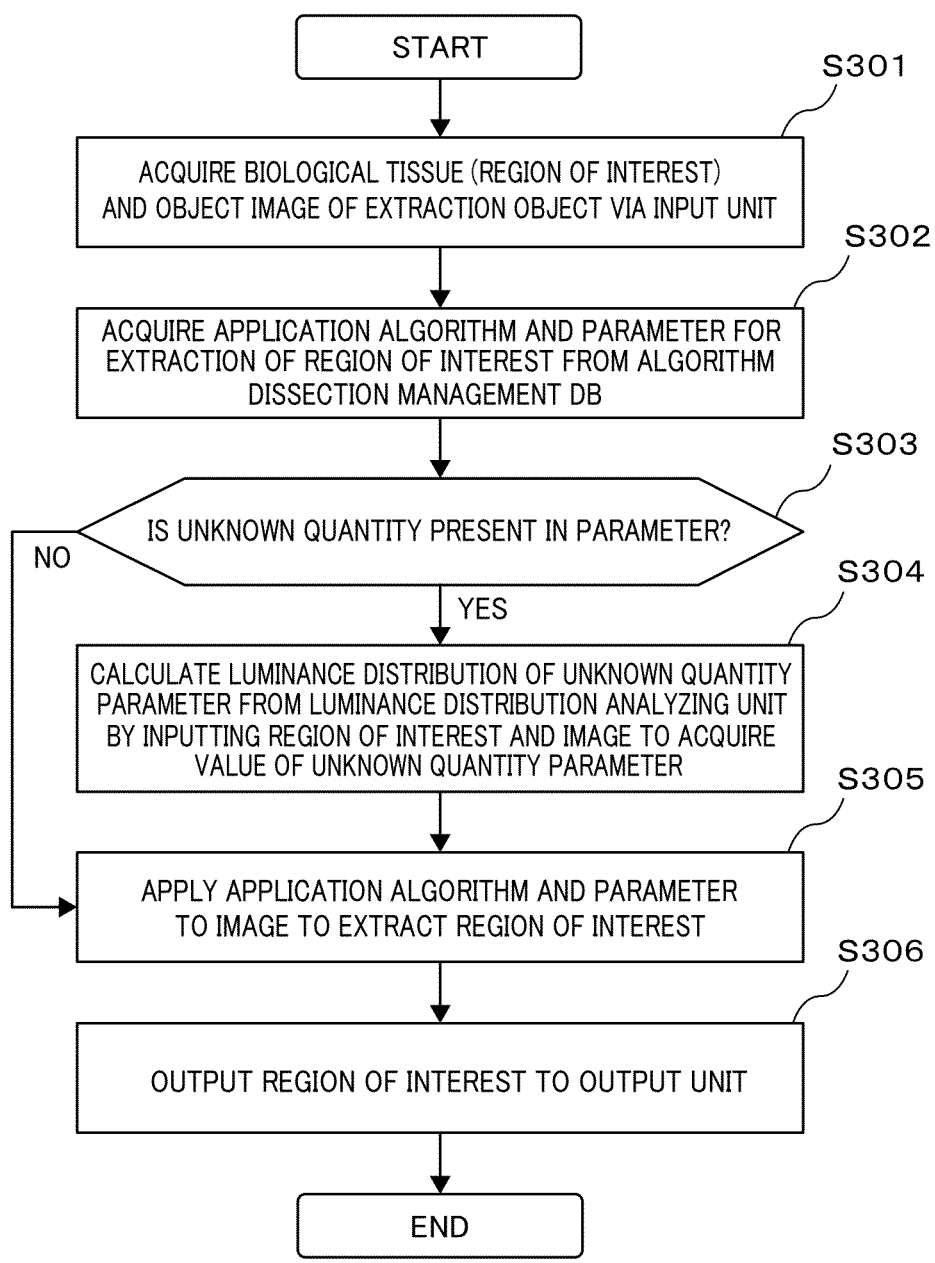
FIG. 3 is a first flowchart showing a flow of processing of the region extraction system in the present invention.
Figure 4:
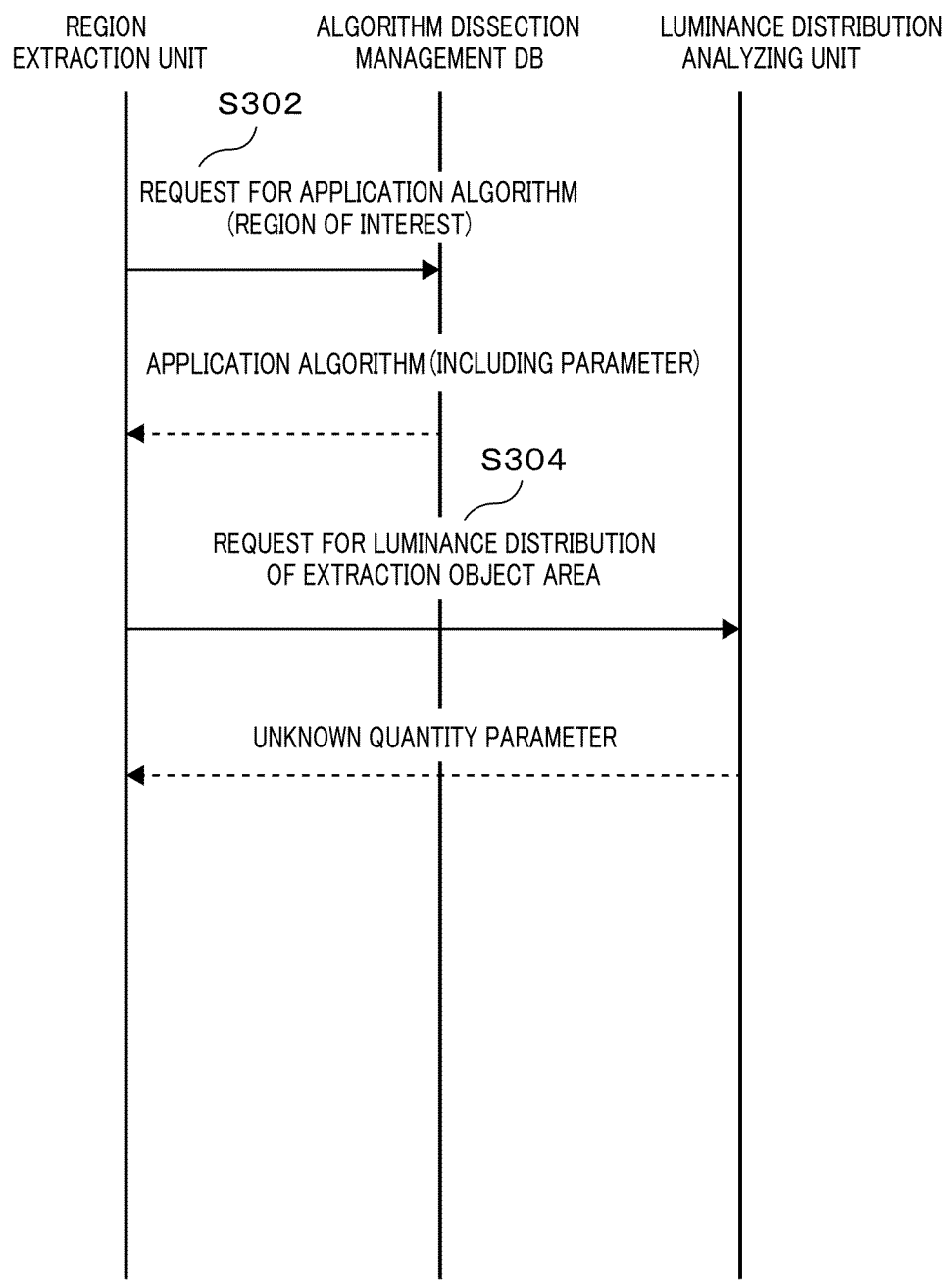
FIG. 4 is a first sequence diagram showing a flow of processing among constitutional elements of the region extraction system in the present invention.
Figure 5:
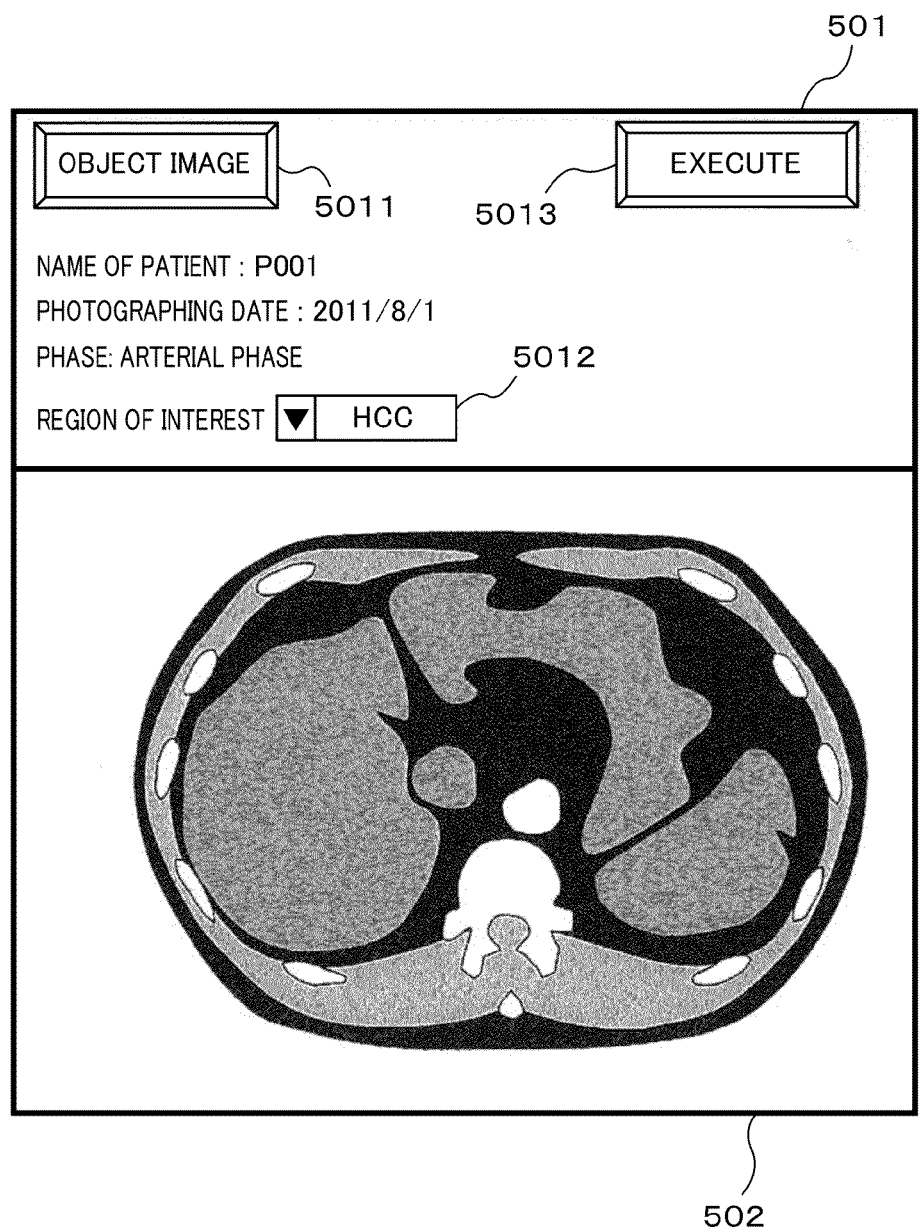
FIG. 5 is a first example showing a screen of the region extraction system in the present invention.

A flowchart showing an operation outline of the region extraction system is shown in FIG. 3. In addition, a sequence diagram pertaining to part (S302 and S304) of the flowchart shown in FIG. 3 is shown in FIG. 4. At first, S301 will be described. In S301, the region extraction unit acquires an ecological tissue (hereinafter, a region of interest) which is an extraction object and an object image via the input unit 101 in order to perform region extraction processing. FIG. 5 shows an example of a screen to be displayed on the display unit 102 in order to describe S301. The screen shown in FIG. 5 is configured by a condition setting unit 501, an object image select button 5011, a region-of-interest select button 5012, an execute button 5013 and an image display unit 502. At first, when the user depresses the object image select button 5011 and selects the object image by selecting a folder of the stored object image, the object image is displayed on the image display unit 502. Next, the region of interest is input via the region-of-interest select button 5012. Finally, when the execute button 5013 is depressed, processing in S302 and succeeding ones is executed and a result of extraction of the region of interest is displayed on the image display unit 502 (S306). In the present embodiment, a state that for the image displayed on the image display unit 502, an HCC (Hepatocellular Carcinoma: hepatocarcinoma) is designated as the region of interest with the region-of-interest select button 5012 is shown.

In S302, the region extraction unit acquires an application algorithm and a parameter from the algorithm dissection management database 104 for extraction of the region of interest. In the first stage in FIG. 4, a state of exchanging messages among system constitutional elements in S302 is expressed by the sequence diagram. Here, an example of the algorithm dissection management database 104 is shown in FIG. 6. In the present embodiment, a state that there are two tables (an algorithm dissection management table 601 and a parameter pattern table 602) in the algorithm dissection management database 104 is shown. The algorithms for extracting the biological tissues and IDs of the parameter patterns thereof are noted in the algorithm dissection management table. In addition, concrete parameters corresponding to the IDs of the parameter patterns are noted in the parameter pattern table. Incidentally, in the parameter pattern table, [−] indicates that a corresponding parameter is not used and [?] indicates that it is an unknown quantity. In the present embodiment, it is seen that the intrahepatic blood vessel, the portal vein and the HCC can be simultaneously extracted by applying the first parameter pattern and Level Set to the image of the arterial phase. In addition, it is seen that in order to extract the HCC alone, one needs only apply the second parameter pattern and Level Set to the object image. In a case where the HCC is the region of interest as shown in FIG. 5, the second parameter pattern and Level Set are acquired in S302.

Figure 7:
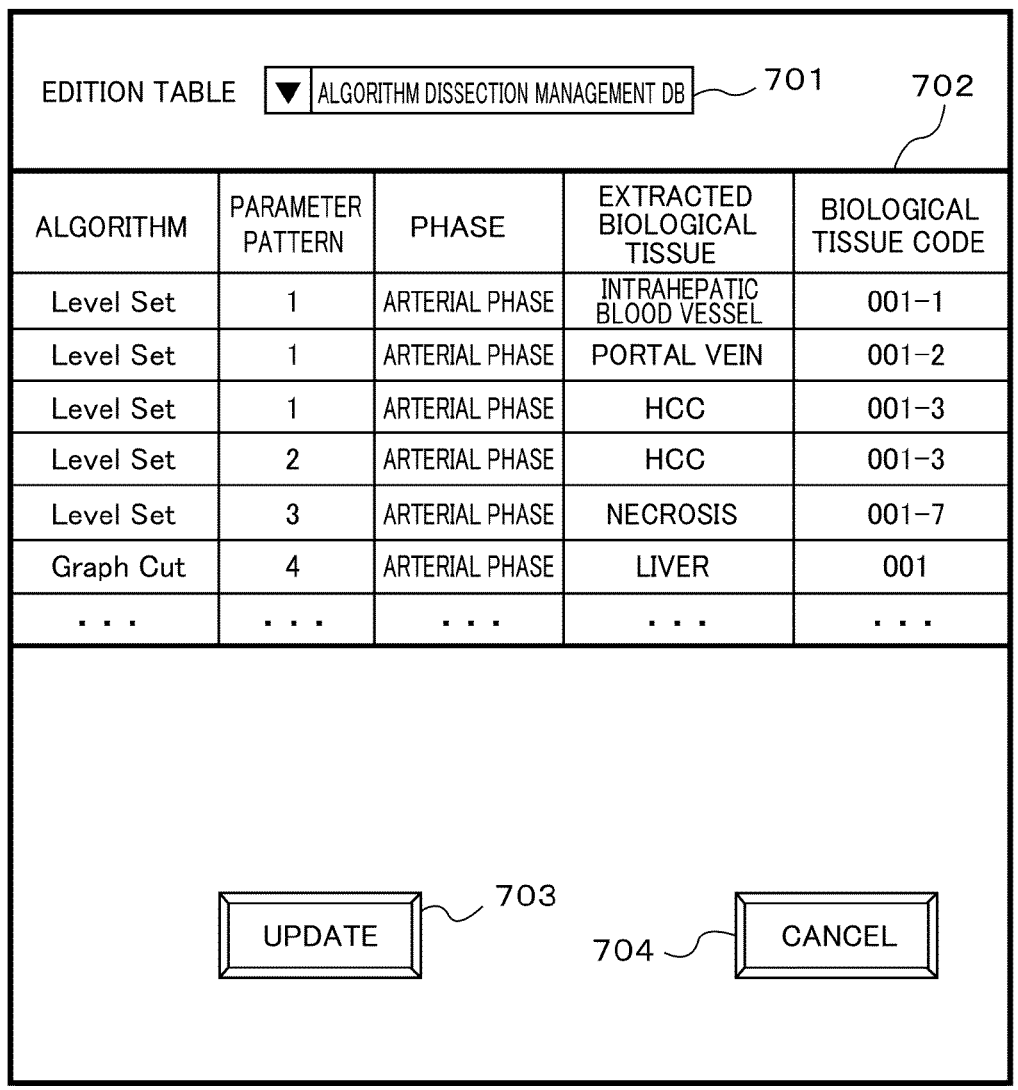
FIG. 7 is a second example showing the screen of the region extraction system in the present invention.

Edition of the algorithm dissection management database 104 by the user is possible. An example of a screen that the contents in the algorithm dissection management database 104 have been displayed on the display unit 102 is shown in FIG. 7. The screen shown in FIG. 7 is configured by an edition table selection area 701, an edition table presentation unit 702, an edition update button 703 and an edition cancel button 704. First, when the user selects a table to be edited via the edition table selection area 701, the object table is displayed on the edition table presentation unit 702. In the present embodiment, a state that the algorithm dissection management table 104 is selected in the edition table selection area 702 and the contents are being displayed on the edition table presentation unit 702 is shown. Although the algorithm dissection management table 104 is selected here, selection and edition of the later described luminance distribution management database 106 are also possible. Next, when edition is terminated via the input unit 101, the edition update button 703 is depressed in a case where the edited contents are to be updated and the edition cancel button 704 is depressed for cancellation. It becomes possible to cope with new knowledge pertaining to the parameters and algorithms by enabling edition of the table in this way. Thereby, there are such advantageous effects that it becomes possible to extract a new biological tissue, the extraction precision is improved and so forth.

In S303, the region extraction unit discriminates whether there exits the unknown quantity in the parameters acquired from the algorithm dissection management database 104, and in a case where there exists the unknown quantity, it proceeds to S304 and in the case of absence, it proceeds to S305. In the present embodiment, in a case where the region of interest is only the HCC as shown in FIG. 5, since there exist the unknown quantities in the parameters (the luminance maximum value and the luminance minimum value) as shown in FIG. 6, it proceeds to S304. In addition, in a case where the region of interest is the liver, since the parameter pattern is switched to 4 and there exists no unknown quantity as shown in FIG. 6, it proceeds to S305.

In S304, the region extraction unit acquires the luminance distribution of the unknown quantity parameter from the luminance distribution analyzing unit with entry of the region of interest and the object image and acquires the value of the unknown quantity parameter. In the second stage in FIG. 4, a state of exchanging the messages among the system constitutional elements in S304 is expressed by the sequence diagram. Input values in S304 are the same as those of the region of interest and the object image acquired in S301. Details of S304 will be described later by using FIG. 8 and so forth.

In S305, the region extraction unit applies the application algorithms and the parameters acquired in S302 and S304 to the object image to extract the region of interest. However, in some cases, the parameter may not be acquired in S304 depending on a result of discrimination in S303. In the present embodiment, in a case where the region of interest is only the HCC as shown in FIG. 5, the region of the HCC is extracted by adapting the third parameter pattern shown in the parameter pattern table in FIG. 6 and the parameter value acquired in S304 to Level Set so as to apply them to the object image.

Here, a basic way of thinking as to processing (S304) of the luminance distribution analyzing unit will be described. When extracting the region, the luminance value distribution of the region concerned is often unknown. For example, in the contrast CT checkup for the HCC, in the arterial phase to be photographed in about 30 seconds after rapid intravenous injection of the contrast medium, the contrast medium is taken into the object tissue and is highly absorbed and the image contrast of the object tissue becomes clear. However, since the contrast medium rapidly diffuses and the photographing timings are often made different, there is no guarantee that the luminance value distributions of the region concerned will be always made the same. Therefore, in prior art, the false positives are increased by extracting the region that the user does not intend and it has caused the deterioration of extraction precision. Accordingly, in the present invention, the possibility that the luminance distribution of the region of interest may be estimated from a result of extraction of the similar area by extracting in advance a biological tissue which is similar to the region of interest in luminance distribution and is readily extracted, in place of obtaining the luminance distribution of the region of interest by using similarity in diffusion of the contrast medium for every biological tissue has been thought about. In the case of the HCC used in the present embodiment, it is difficult to grasp the accurate luminance value distribution before extracting the HCC as ever described. However, since the intrahepatic blood vessel, the portal vein and the HCC are the same in diffusion characteristic of the contrast medium in the arterial phase, when extraction of these biological tissues is readily performed, these ecological tissues are extracted in advance. The luminance distribution of the HCC which is the region of interest is estimated from a result of extraction so performed to determine the luminance maximum value and the luminance minimum value.

Figure 8:
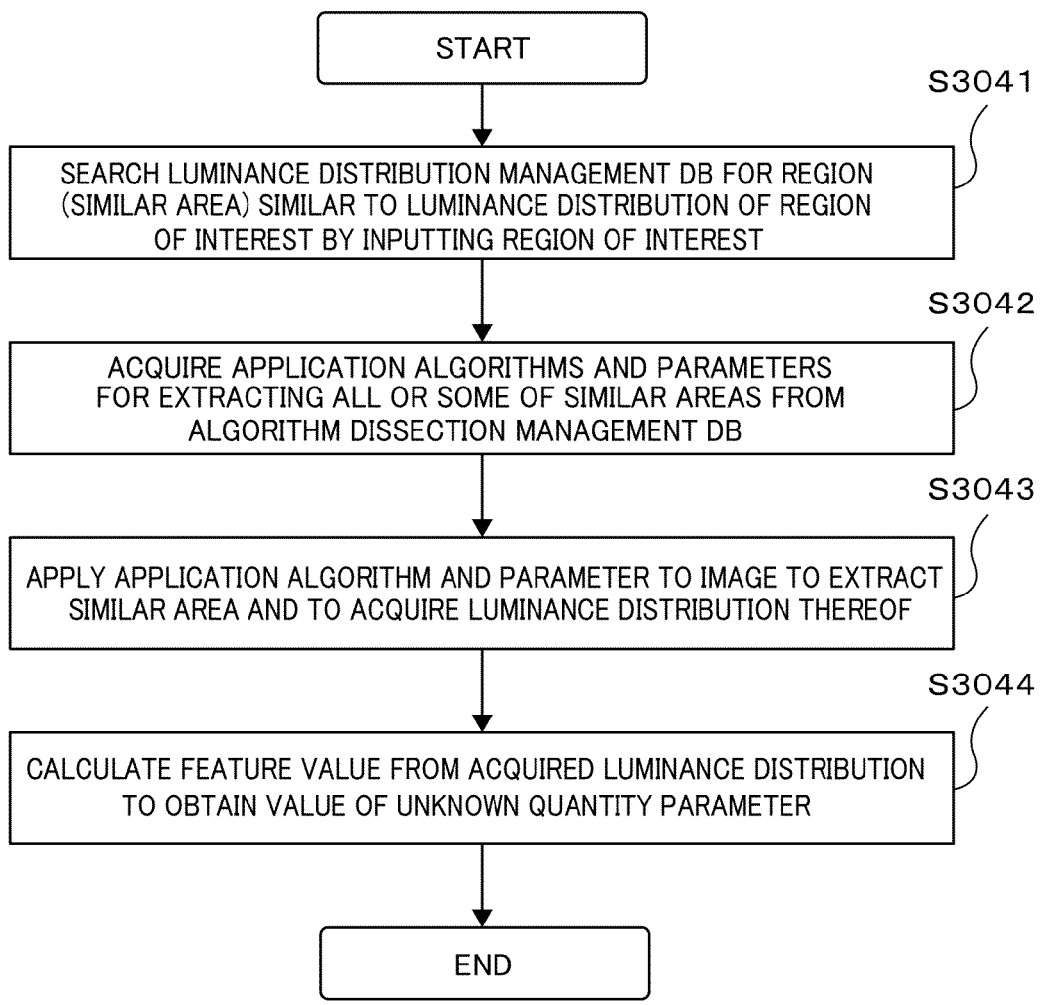
FIG. 8 is a first flowchart showing a flow of processing in a luminance distribution analyzing unit in the region extraction system in the present invention.
Figure 9:
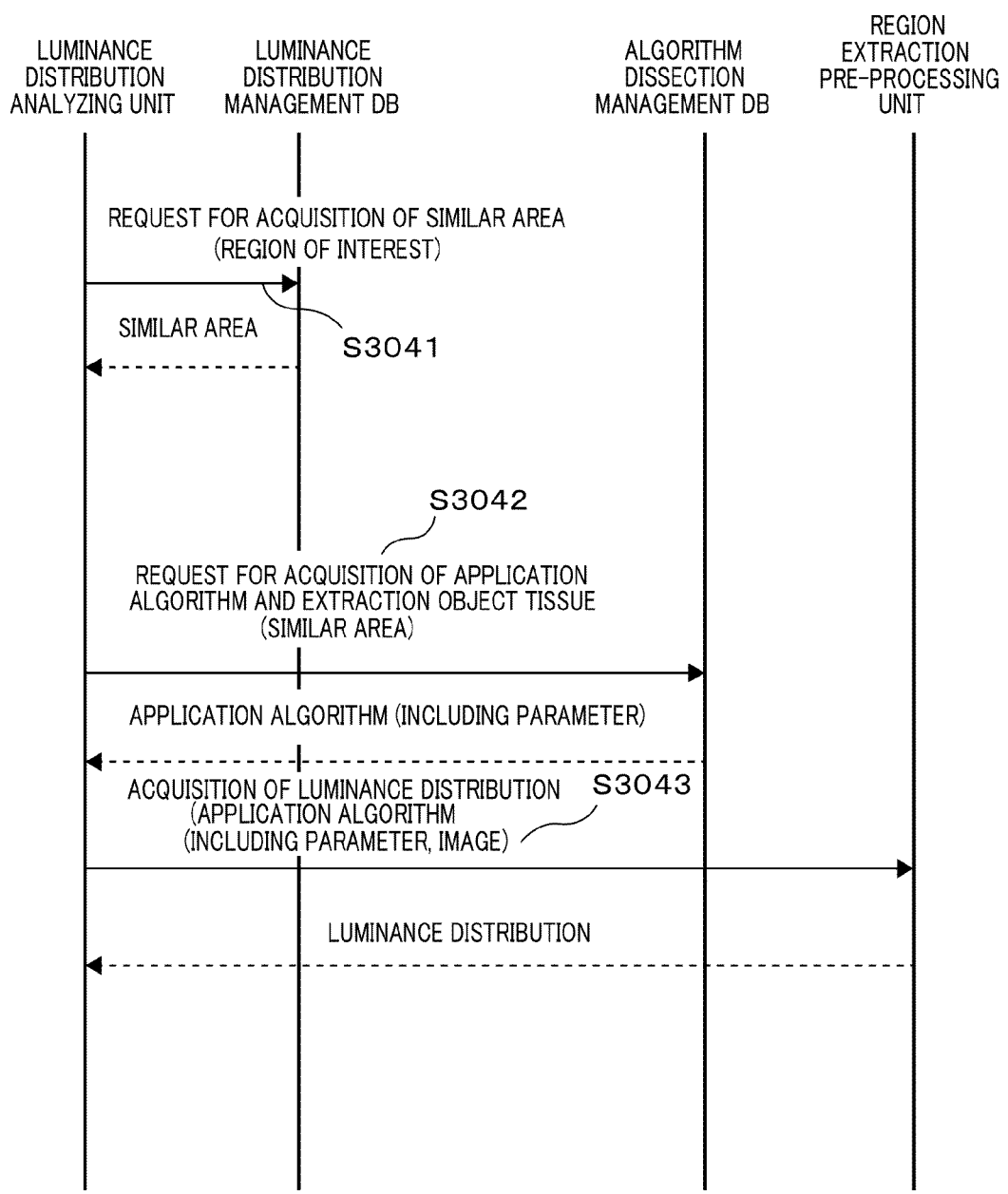
FIG. 9 is a first sequence diagram showing a flow of processing among the constitutional elements which coordinate with the luminance distribution analyzing unit in the region extraction system in the present invention.

Next, detailed processing (S304) of the luminance distribution analyzing unit will be described by using FIG. 8, FIG. 9 and FIG. 10. A flowchart showing details of the luminance distribution analyzing unit is shown in FIG. 8. In addition, a sequence diagram pertaining to part (S304, S3042 and S3043) of the flowchart shown in FIG. 8 is shown in FIG. 9.

In S3041, the luminance distribution analyzing unit searches the luminance distribution management database 106 for the region (the similar area) which is similar to the luminance distribution of the region of interest with entry of the region of interest. In the first stage in FIG. 9, a state of exchanging the messages among the system constitutional elements in S3041 is expressed by the sequence diagram. The luminance distribution management database 106 manages the regions which are similar in luminance distribution. Here, an example of the luminance distribution management database 106 is shown in FIG. 10. In the present embodiment, a state that the regions which are similar in luminance distribution are managed for every phase such as the arterial phase, a delayed phase and so forth and the intrahepatic blood vessel, the portal vein, the HCC and the kidney have the similar luminance distributions in the arterial phase is shown. Incidentally, since, in some cases, the luminance values are different depending on device manufactures, "Device Manufacturer" may be added to the field of the luminance distribution management database 106. Here, a concrete example of processing details in S3041 in extraction of the HCC shown in FIG. 5 will be described. In the present example, when that the HCC is to be extracted from the image in the arterial phase is accepted as the input, the four biological tissues of the intrahepatic blood vessel, the portal vein, the HCC and the kidney are extracted from the luminance distribution management table 106 shown in FIG. 10 as the similar areas of the HCC. Here, although only the region of interest is input in S3041, in a case where the similarity in luminance distribution is managed in accordance with the phase as in the luminance distribution management table shown in FIG. 10, also the phase is included as the input in S3041. However, the phase is not always an essential input item.

In S3042, the luminance distribution analyzing unit acquires sets of the application algorithms and the parameters for extracting all or some of the similar areas from the algorithm dissection management database 104. When acquiring them, the sets including no unknown quantity in the parameters are acquired in order to implement ready extraction. In the second stage in FIG. 9, a state of exchanging messages among the system constitutional elements in S3042 is expressed by the sequence diagram. In the present embodiment, the application algorithms and the parameters for extracting the intrahepatic blood vessel, the portal vein, the HCC and the kidney which have been extracted as the similar areas in S3041 are acquired from the algorithm dissection management database 104 shown in FIG. 6. In the present example, it becomes possible to extract the intrahepatic blood vessel, the portal vein and the HCC which are some of the similar areas by applying the first parameter and Level Set to the object image. Thus, in S3042, the first parameter and Level Set are acquired.

In S3043, the luminance distribution analyzing unit applies the application algorithms and the parameters so acquired in S3042 to the object image, extracts the similar areas and acquires the luminance distributions thereof. In the third stage in FIG. 9, a state of exchanging messages among the system constitutional elements in S3043 is expressed by the sequence diagram. In the present embodiment, the intrahepatic blood vessel, the portal vein and the HCC which are the similar areas are extracted and the luminance distributions thereof are acquired by applying the first parameter and Level Set acquired in S3042 to the object image.

In S3044, the luminance distribution analyzing unit calculates an image feature value from the luminance distribution acquired in S3043 to set it as a value of the unknown quantity parameter. As a method of calculating the image feature value from the luminance distribution, a method of obtaining it from a maximum value and a minimum value of the luminance distribution, a method of obtaining it from a mean value/a median value/a mode of the luminance value/a variance value and so forth are available. For example, in the present embodiment, the luminance value (hereinafter, the mode) that the number of pixels is set to the mode and the variance value are obtained in the luminance distributions of the intrahepatic blood vessel, the portal vein, the HCC and the kidney acquired in S3043, the mode of the luminance value+ the variance value is set as the luminance maximum value and the mode of the luminance value is set as the luminance minimum value.

It becomes possible to estimate the luminance value distribution of the region of interest with higher precision by using the luminance value distribution in the region which is similar to it in luminance value and is readily extracted by the region extraction system by such image data analysis processing and, thereby, it becomes possible to overcome the problem of false positives in region extraction. Thereby, it becomes possible to facilitate region extraction and to implement more accurate region extraction. That is, it becomes possible to reduce the labor of the doctor in tumor diagnosis.

Embodiment 2

Figure 11:
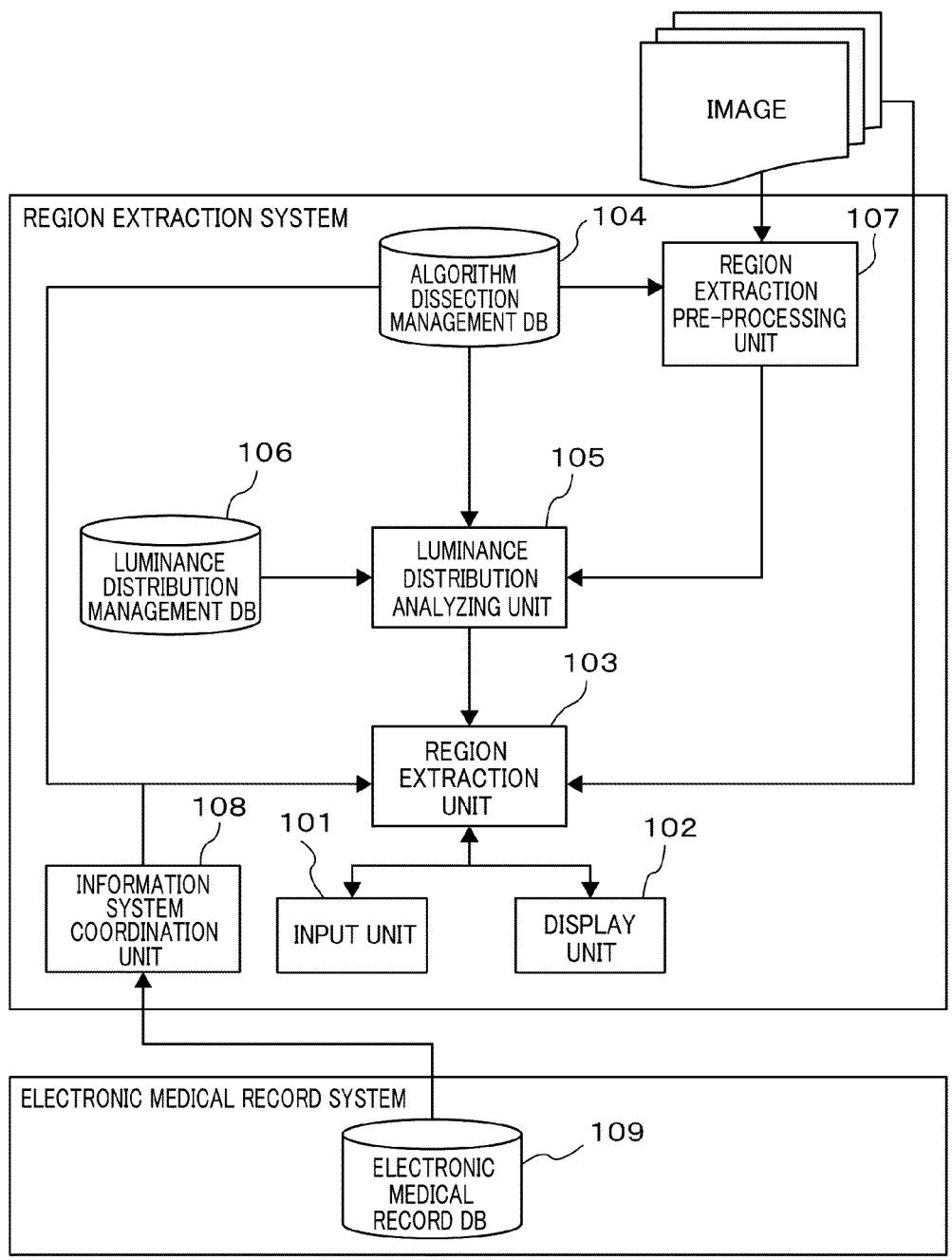
FIG. 11 is a second configuration diagram of the region extraction system in the present invention.

FIG. 11 is a second configuration diagram of the region extraction system in the present invention. The processing method of the region extraction unit 103 is altered by newly adding an information system coordination unit 108 to the configuration diagram shown in FIG. 1 particularly for the purpose of acquiring the region of interest by coordinating with another information system such as the electronic medical record system and so forth. Although in the present embodiment, it coordinates with the electronic medical record system, it may coordinate with a system that manages the region of interest such as a radiological information system and so forth. The information system coordination unit 108 can implement various kinds of processing by developing/starting the predetermined program in the central processing unit 2013, the memory 2012 and so forth shown in FIG. 2. In addition, in FIG. 11, the electronic medical record system has at least an electronic medical record database 109 and the electronic medical record database 109 is configured by the external storage and so forth represented by the HDD (Hard Disk Drive) device.

Figure 12:
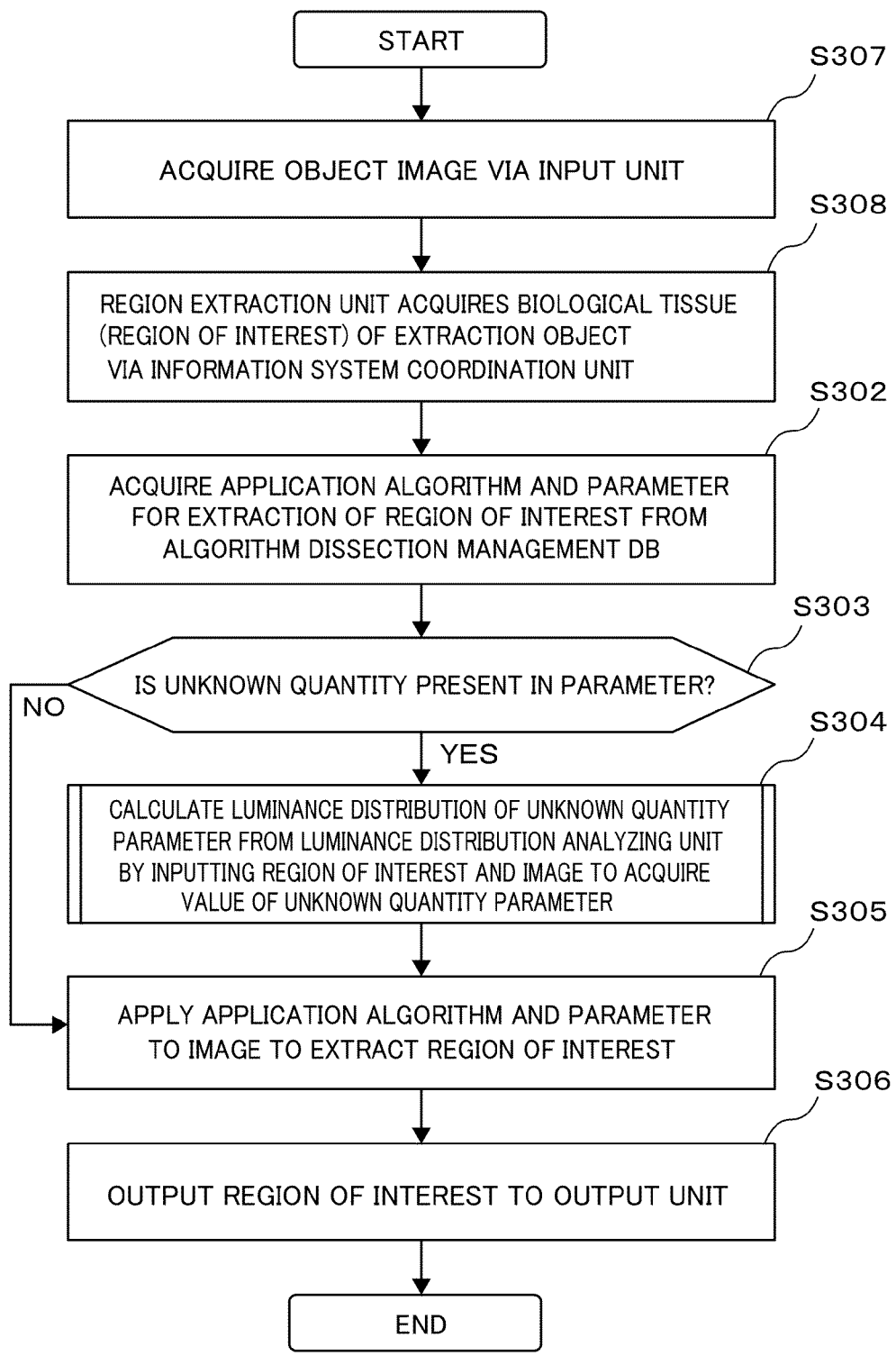
FIG. 12 is a second sequence diagram showing a flow of processing among the constitutional elements of the region extraction system in the present invention.

A flowchart that implements the system shown in the present embodiment is shown in FIG. 12. As for the difference between it and the flowchart shown in FIG. 3, it is different in the point that although the region of interest has been acquired via the input unit (S301) in FIG. 1, it has been acquired via the information system coordination unit (S307 and S308) in FIG. 12. Therefore, the present processing will be described in detail.

Figure 14:
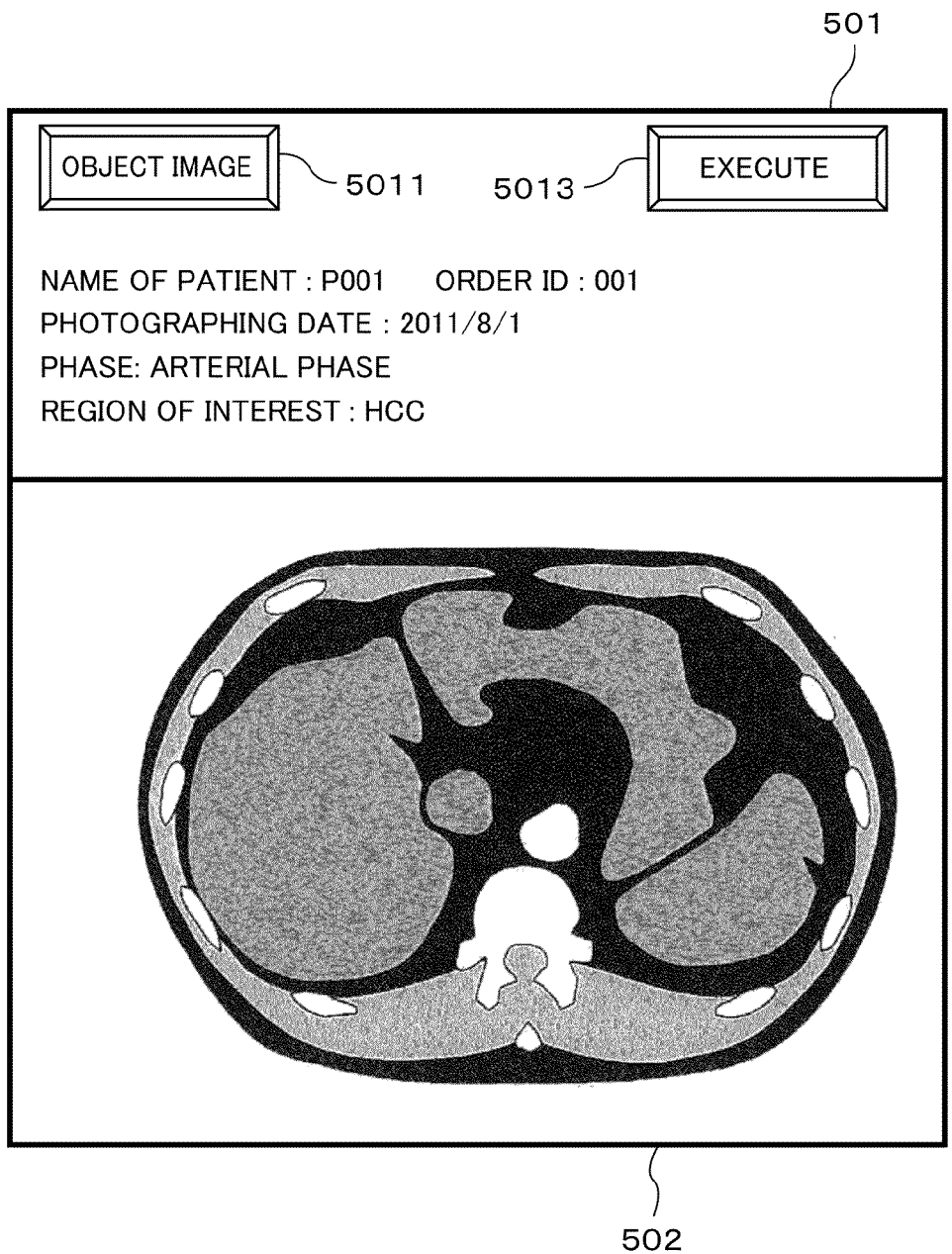
FIG. 14 is a third example showing the screen of the region extraction system in the present invention.

In S307, only the object image is acquired via the input unit 101 in order to perform region extraction processing. Next, in S308, the region extraction unit 103 acquires the region of interest which is the extraction object from the database in the information system such as the electronic medical record system and so forth via the information system coordination unit 108. An example of the electronic medical record database 109 is shown in FIG. 13. In the present embodiment, a state that an order management table that holds order information in the electronic medical record system is present in the electronic medical record database 109 is shown. In the present example, a state that in the order of an order ID of 001, Mr. Ada Bo is suspicious of the HCC in the liver of a patient P001 and orders to take pictures on 2011/07/1 is shown. An example of a screen which is relevant to S307 and S308 and is to be displayed on the display unit 102 is shown in FIG. 14. It is different from the one in FIG. 5 in the point that there is no region-of-interest select button 5012.

Next, a flow of processing shown in FIG. 12 will be described by using FIG. 13 and FIG. 14 and using a concrete example. In the present embodiment, first, when the object image select button 5011 shown in FIG. 14 is depressed and the object image is selected by selecting the folder of the stored object image by the user, the name of the patient, the order ID, the photographing date and the phase are acquired and the object image is displayed on the image display unit 502 (S307). Next, when the execute button 5013 is depressed by the user, the region extraction unit 103 acquires the region of interest as the HCC from the names of suspicious diseases in the order management table shown in FIG. 13 (S308). Thereafter, the HCC which has been acquired as the region of interest is displayed on the screen shown in FIG. 14 and the region extraction processing is performed simultaneously therewith (S302 to S305), and a final result is displayed (S306).

It becomes possible to acquire the name of the area which will be the region concerned as the region of interest by the region extraction system by such image data analysis processing with no intervention of the user. Thereby, it becomes possible to further reduce the load on the user.

Embodiment 3

Figure 15:
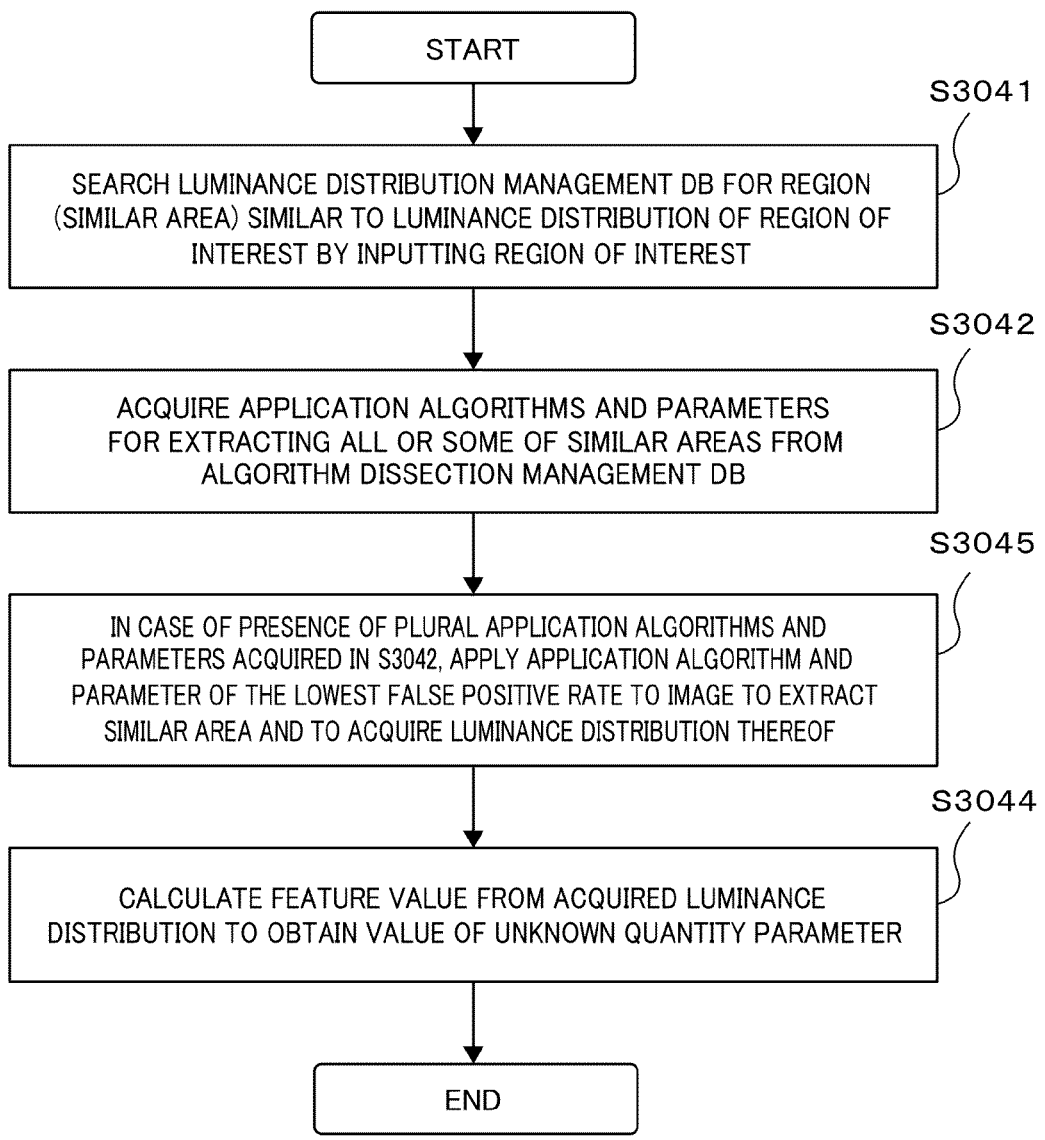
FIG. 15 is a second flowchart showing a flow of processing in the luminance distribution analyzing unit in the region extraction system in the present invention.]

FIG. 15 is a second flowchart showing detailed processing (S304) of the luminance distribution analyzing unit 105 in the present invention. Comparing it with the flowchart shown in FIG. 8, the processing of S3043 is replaced with that of S3045 in order to cope with a situation that there exist plural choices of algorithms and parameters to be acquired from the algorithm dissection management database 104. Thus, a flow of processing focusing on S3045 will be described by using a concrete example of the algorithm dissection management database 104 shown in FIG. 16. First, in S3042, in a case where the region of interest is the HCC, sets of the application algorithms and the parameter patterns for extracting the intrahepatic blood vessel, the portal vein and the HCC and sets of the application algorithms and the parameter patterns for extracting the intrahepatic blood vessel and the portal vein are acquired from the algorithm dissection management database 104 shown in FIG. 16.

Next, in S3045, in a case where there exist a plurality of sets of the application algorithms and the parameters acquired in S3042, the set of the application algorithm and the parameter which is the lowest in false positive rate is applied to the image. Thereby, the similar area is extracted and the luminance distribution thereof is acquired. This is because the precision is improved by taking the incidence of false positives into account and the more accurate luminance distribution of the region of interest can be acquired. In the present embodiment, the false positive rate is minimized when the application algorithms and the parameters for extracting the intrahepatic blood vessel and the portal vein are used. For this purpose, the intrahepatic blood vessel and the portal vein which are the similar areas are extracted and the luminance distributions thereof are acquired by applying the fifth parameter and Level Set to the object image.

Finally, in S3044, the image feature value is calculated from the luminance distributions acquired in S3045 and it is set as a value of the unknown quantity parameter. For example, in the present embodiment, a minimum value a in positive integers that the number of pixels having the luminance values within a closed space that the mode of the luminance distributions of the intrahepatic blood vessel and the portal vein acquired in S3045, a mode −a and a mode +a are set as endpoints exceeds a threshold value which has been set in advance is calculated as the image feature value. The luminance maximum value of the unknown quantity parameter is determined as the mode +a and the luminance minimum value thereof is determined as the mode −a.

It becomes possible to take the incidence of false positives into account, the more accurate luminance distribution can be estimated and the extraction precision of the region of interest is improved by the region extraction system by such image data analysis processing.

Embodiment 4

Figure 17:
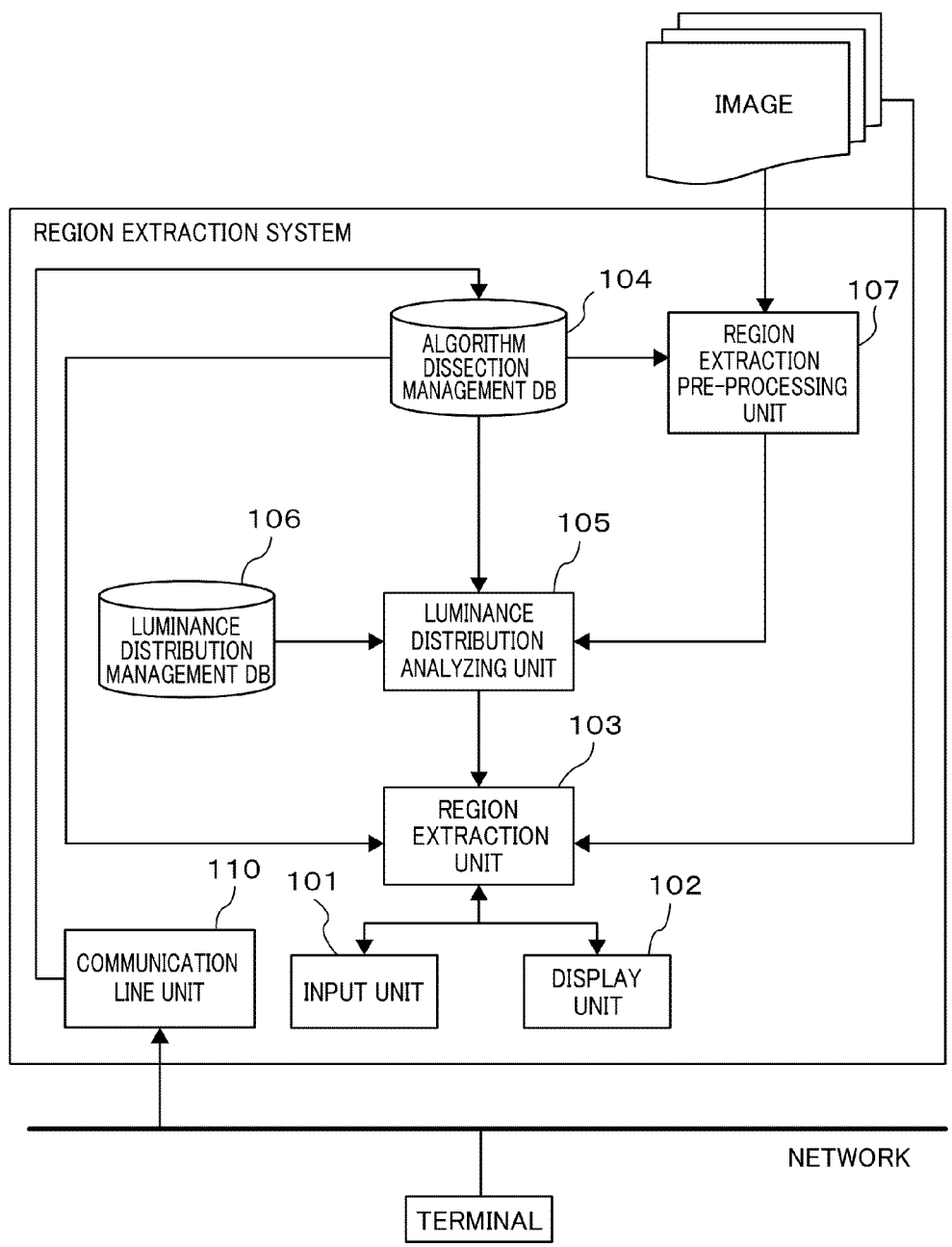
FIG. 17 is a third configuration diagram of the region extraction system in the present invention.
Figure 18:
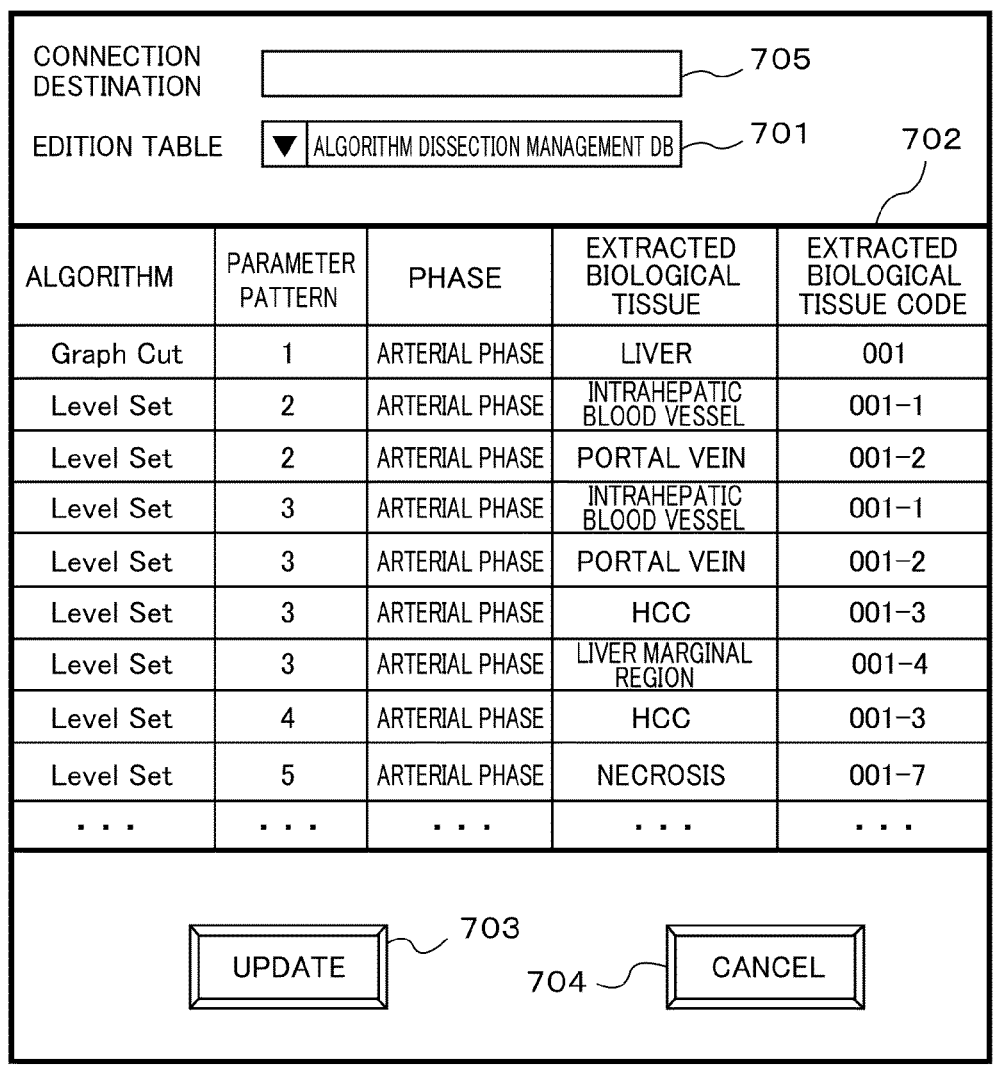
FIG. 18 is an example showing a screen that the algorithm dissection management database of the region extraction system in the present invention has been displayed on another system.

FIG. 17 is a configuration diagram of the region extraction system in the present invention. A communication line unit 110 is added to the configuration diagram shown in FIG. 1, in particular, for the purpose of remotely editing the algorithm dissection management database 104. The communication line unit 110 can implement various kinds of processing by developing/starting the predetermined program in the central processing unit 2013, the memory 2012 and so forth shown in FIG. 2. In the communication line unit 110, information stored in the algorithm management dissection database 104 is distributed to another information system such as the electronic medical record, a radiological information system and so forth via a communication line and the contents edited by another information system are accepted via the communication line. An example of a screen which has been displayed on a display unit of another information system via the communication line unit 110 is shown in FIG. 18. The difference between it and the one in FIG. 7 lies in the point that a connection destination designation area 705 has been newly added in order to coordinate with the region extraction system. First, when the user selects a table to be edited via an edition table selection area 701 and designates a place such as an IP address and so forth of the region extraction system which is a coordination object in the connection destination designation area 705, the object table is displayed on an edition table presentation unit 702 via the communication line unit 110. Next, when edition is terminated, an edition update button 703 is depressed in a case of updating edited contents and an edition cancel button 704 is depressed for cancellation. Thereby, the algorithm dissection management database 104 is updated via the communication line unit 110.

Since it becomes possible to remotely edit the algorithm dissection management database 104 by the region extraction system by such image data analysis processing, in a case where an algorithm and a parameter which would enable to extract a new biological tissue have been found, prompt reflection thereof on the region extraction system becomes possible. In addition, there is no need to go to a field that the region extraction system sets and remote maintenance becomes possible by remotely editing it.

INDUSTRIAL APPLICABILITY

The present invention pertains to the analysis processing system for medical image data and is useful as the image data analysis processing technology, in particular, in order to assist in accurate region extraction.

REFERENCE SIGNS LIST

101: input unit
102: display unit

103: region extraction unit
104: algorithm dissection management database
105: luminance distribution analyzing unit
106: luminance distribution management database
107: region extraction pre-processing unit
108: information system coordination unit
109: electronic medical record database
110: communication line unit
2010: keyboard
2011: liquid crystal display
2012: memory
2013: central processing unit
2014: external storage
501: condition setting unit
5011: object image select button
5012: region-of-interest select button
5013: execute button
502: image display unit
701: edition table selection area
702: edition table presentation unit
703: edition update button
704: edition cancel button
705: connection destination designation area

The invention claimed is:

1. A system that extracts a region of interest from an image, the region extraction system, having:
an input unit that accepts inputs of the region of interest and an object image;
an algorithm management dissection database that stores an optimum algorithm and an unknown quantity including parameter for extracting the region of interest;
a region extraction unit that acquires the algorithm and the parameter stored in the algorithm management dissection database with entry of the region of interest and the object image and executes region extraction processing for the region of interest by applying the algorithm and the parameter so acquired to the object image;
a luminance distribution analyzing unit that outputs an unknown quantity parameter by calculating a luminance distribution of the region of interest with entry of the region of interest and the object image;
a luminance distribution management database that stores similarity in luminance distribution of biological tissues;
a region extraction pre-processing unit that performs pre-processing for obtaining the unknown quantity parameter with entry of the object image, and the algorithm and the parameter stored in the algorithm management dissection database; and
a display unit that displays a result of extraction,
wherein in the region extraction unit, in a case where the unknown quantity is included in the parameter so input, an optimum value of the parameter is acquired from the luminance distribution analyzing unit.

2. The region extraction system according to claim 1, further having:
an information system coordination unit that acquires the region of interest from an electronic medical record database or a radiological information system database.

3. The region extraction system according to claim 1, wherein further in the luminance distribution analyzing unit,
regions having luminance distributions similar to the luminance distribution of the region of interest are searched for as similar areas from the similarity stored in the luminance distribution management database, and
the algorithms and the parameters used for extracting all or some regions of the similar areas are acquired from the algorithm management dissection database,
in the region extraction pre-processing unit, as pre-processing for obtaining the unknown quantity parameter, the region of the similar area is extracted by using the algorithm and the parameter so acquired and an image feature value is calculated by using the luminance distribution calculated from a result of region extraction, and
a value of the unknown quantity parameter is determined from the image feature value.

4. The region extraction system according to claim 3, wherein further
a false positive rate which is a probability that a false positive occurs is stored for every set of the algorithm and the parameter in the algorithm management dissection database, and
in the luminance distribution analyzing unit, in a case where there exists a plurality of the similar areas similar to the luminance distribution of the region of interest, only the algorithm and the parameter which are the smallest in false positive rate are acquired from the algorithm management dissection database by using data in the algorithm management dissection database.

5. The region extraction system according to claim 3,
wherein further the parameter of the unknown quantity acquired by the region extraction unit is a luminance maximum value and a luminance minimum value of the region of interest, and
in the luminance distribution analyzing unit,
the image feature value used for determining the unknown quantity parameter in the region extraction pre-processing unit is a minimum value a of positive integers that the number of pixels having luminance values in a closed space that a luminance value with which the number of pixels is set to a mode in the luminance distribution calculated by the region extraction pre-processing unit, a mode −a and a mode +a are set as endpoints exceeds a threshold value which has been set in advance.

6. The region extraction system according to claim 1,
wherein further the data stored in the algorithm management dissection database is displayed on the display unit, and
edited contents of the algorithm management dissection database displayed on the display unit are accepted by the input unit.

7. The region extraction system according to claim 1, further having:
a communication line unit that distributes information stored in the algorithm management dissection database to another information system via a communication line and accepts edited contents of the algorithm management dissection database edited by another information system via the communication line.

8. The region extraction system according to claim 2,
wherein further the data stored in the algorithm management dissection database is displayed on the display unit, and
edited contents of the algorithm management dissection database displayed on the display unit are accepted by the input unit.

9. The region extraction system according to claim 2, further having:
a communication line unit that distributes information stored in the algorithm management dissection database to another information system via a communication line and accepts edited contents of the algorithm management dissection database edited by another information system via the communication line.

\* \* \* \* \*